United States Patent
Ahlnäs et al.

[11] Patent Number: 5,811,082
[45] Date of Patent: Sep. 22, 1998

[54] SOLID PROTECTOR AGAINST UV, PROCESS FOR ITS PREPARATION AND USE THEREOF

[75] Inventors: John Thomas Ahlnäs, Helsinki; Timo Valdemar Löfgren, Espoo, both of Finland

[73] Assignee: Kemira Pigments Oy, Pori, Finland

[21] Appl. No.: 557,125

[22] PCT Filed: Jun. 2, 1994

[86] PCT No.: PCT/FI94/00232

§ 371 Date: May 8, 1996

§ 102(e) Date: May 8, 1996

[87] PCT Pub. No.: WO94/28867

PCT Pub. Date: Dec. 22, 1994

[30] Foreign Application Priority Data

Jun. 3, 1993 [FI] Finland ..................................... 932529
Mar. 17, 1994 [FI] Finland ..................................... 941270

[51] Int. Cl.⁶ ............................ A61K 7/42; A61K 47/00; C01G 23/047
[52] U.S. Cl. ............................ 424/59; 423/610; 424/400; 424/401; 428/402; 514/772
[58] Field of Search ............................... 424/59; 423/610; 514/772; 428/402

[56] References Cited

FOREIGN PATENT DOCUMENTS

| | | |
|---|---|---|
| 0 385 763 A2 | 9/1990 | European Pat. Off. . |
| 0 418 443 A1 | 3/1991 | European Pat. Off. . |
| 0 433 086 A1 | 6/1991 | European Pat. Off. . |
| 0 523 294 A1 | 1/1993 | European Pat. Off. . |
| 0 535 972 A1 | 4/1993 | European Pat. Off. . |
| 1 006 100 | 4/1957 | Germany . |
| 1 592 865 | 2/1971 | Germany . |
| 3 824 999 A1 | 2/1989 | Germany . |
| 2 206 339 | 1/1989 | United Kingdom . |
| WO 93/00065 | 1/1993 | WIPO . |
| WO 93/11742 | 6/1993 | WIPO . |

*Primary Examiner*—Shelley A. Dodson
*Attorney, Agent, or Firm*—Gary M. Nath; Suet M. Chong; Nath & Associates

[57] ABSTRACT

A less dusty, more stable and more easily handlable protector against UV light than previously is obtained by supplying it in the form of solid particles having a mean diameter of at minimum 10 $\mu$m and containing, dispersed in 90-20 parts by weight of wax, 10–80 parts by weight of a pigment which reduces the penetration UV light and is made up of metal oxide particles of a mean primary particle diameter smaller than 0.150 $\mu$m.

47 Claims, No Drawings

SOLID PROTECTOR AGAINST UV, PROCESS FOR ITS PREPARATION AND USE THEREOF

The invention relates to a solid protector against UV light, comprising a pigment made up of metal oxide particles reducing the penetration of UV light and having an average primary particle diameter smaller than 0.150 μm. Such solid protectors against UV light are used in the cosmetics industry. The invention also relates to the preparation and use of such a solid protector against UV light.

The penetration of harmful ultraviolet radiation into the skin or other material is prevented according to state-of-the-art technology by using both organic and inorganic protectors against UV radiation. Inorganic UV-protectors include many very fine-grained metal oxides. Corresponding metal oxides are in general also available in pigment grades, in which case they reflect or absorb mainly within the wavelength of visible light. Metal oxides protecting from UV radiation deviate from these pigments in that they are transparent to the wavelength of visible light but, instead, reflect or absorb ultraviolet light. They are called UV-pigments. The diameter of the primary particles of UV-pigments is clearly smaller than that of corresponding pigment particles (for example, 0.1-fold), and the interface of their primary particles is considerably larger (for example 100-fold). UV-pigments are often also called "microcrystalline" pigments of "micropigments".

Known inorganic UV-pigments include fine-grained titanium dioxides. The diameter of their primary particles is in the order of 0.020 μm (0.010–0.100 μm), whereas the crystal size of pigment-grade titanium dioxide is in the order of 0.200 μm (0.160–0.250 μm). UV titanium dioxide can be prepared, for example, by the method of publication EP-A-0 444 798 (Kemira Oy), by methods referred to therein, or by other methods. UV titanium dioxide is available in anatase or rutile form or in amorphous form, and its particle shape is round, oblong or needle-like. UV titanium dioxide is available both coated and uncoated, the coatings being either hydrophilic or hydrophobic.

Zinc oxide as a UV-pigment is known from the publication GB 21 84 356 (Kao Corporation). Other known UV-pigments include oxides of cerium, zirconium and iron, having particle sizes below 0.150 μm and absorbing UV light. There are also known photochromatic UV-pigments in which the ability to protect against light-increases under the effect of UV radiation (EP 526712, Kao Corporation).

Though UV-pigments, when dry, are at least partly agglomerated, their particle size is, nevertheless, so small that the products are highly dust-producing, from which there follow many drawbacks. The working of such a very fine-grained UV-pigment into a well dispersed suspension is often difficult.

The dust problem has been solved in patent publication GB 22 06 339 (Tioxide Group PLC) with respect to UV titanium dioxide by grinding it in an oil phase with the help of an organic dispersing agent in a bead mill. A corresponding method for UV-zinc oxide is known from patent publication EP-A 1-535 972 (Tioxide Specialties Ltd.).

However, the products thus obtained still have deficiencies, of which we mention limited storage stability, need for dispensing devices and for transportation and storage containers, need to mix the stored product or product container, such as a barrel, before dispensing, as well as difficulty of cleaning the said equipment and need to treat the waste slurry produced in their washing. In general it is also necessary to add preservatives to suspension-form UV-pigment dispersions in order to combat microbial growth, even if it would be desirable to have the product keep entirely without preservatives, or at least with substantially smaller preservative doses.

Solid or semi-solid color pellets intended for cosmetics products are known from patent publication PCT 93/00065 (Boots). This invention makes it possible to select a lipstick color from a large number of lipstick color shade alternatives by mixing equal-sized color pellets with an oil mixture, in a numerical quantity ratio indicated by a certain formula, and then by preparing lipsticks from these. The pellets contain a wax component 1–50%, an oil or fat component 30–65%, and pigment or mother-of-pearl 10–35%. The pigments are color pigments conventionally used in lipsticks, such as iron oxide, titanium dioxide, substrate colors, ultramarines, and organic colors. The use of UV-pigment is not specifically mentioned; it is stated that, in addition to gloss control agents, skin-calming agents, skin-care agents, vitamins, preservatives and antioxidants, the products may also contain sun-protectors.

The object of the present invention is to eliminate the problems of dust and stability mentioned above by providing a dust-free and stabile solid protector against UV light, less susceptible to microbes, the protector being based on the said metal oxide particles less than 0.150 μm in size and being mainly characterized in what is stated in the characterizing clause of claim 1. It has thus been-realized, that a dust-free and stable UV-protector is obtained if it is in the form of solid particles, having a minimum diameter of 10 μm and containing the said pigment reducing the penetration of UV light, dispersed in 90-20 parts by weight of wax.

The pigment reducing the penetration of UV light used in the solid UV-protector according to the invention may be any pigment reducing the penetration of UV light, the pigment being made up of metal oxide particles having a mean primary particle diameter smaller than 0.150 μm. Typical usable metal oxide particles include the oxides of titanium, cerium, zirconium, iron, and zinc. The crystal form of the oxides may vary greatly, but all of these metal oxides are characterized in that the mean diameter of their primary particles is smaller than 0.150 μm. A preferred mean diameter of the primary particles is 0.010–0.100 μm, and the most preferred in the order of approx. 0.020 m. It is also possible to use photochromatic UV-pigments in which the ability to protect against light increases under the effect of UV radiation. Such pigments have been disclosed, for example, in publication EP 526 712, which publication is appended hereto as a reference.

As was pointed out above, the UV-protector according to the invention is obtained by dispersing 10–80 parts by weight of a pigment reducing the penetration of UV light into 90-20 parts by weight of wax. By parts by weight is meant in this context the weight ratio between the pigment reducing the penetration of UV light and wax, in which case there may be present any amount of other components, as long as the formed UV-protector will remain solid and in particle form. By the words "disperse" and "dispersion" is meant the maximally fine distribution of at least one substance, in this case a pigment reducing the penetration of UV light, into another, continuous phase, i.e. in this case wax. By maximally fine distribution is in this case also meant an even distribution into the continuous phase, i.e. wax.

Preferably the proportion of the pigment which reduces the penetration of UV light is at minimum 36% by weight, more preferably at minimum approx. 40% by weight, and most preferably at minimum approx. 44% by weight, of the whole UV-protector. The UV-protector preferably contains the said pigment which reduces the penetration of UV light in an amount of at maximum 85% by weight, more preferably at maximum 80% by weight, and most preferably at maximum 75% by weight.

As was pointed out, the solid UV-protector according to the invention is in the form of solid particles having a mean diameter of at minimum 10 μm. In this manner there is obtained a dust-free, stable and easily handled material, which can easily be added to various products in which it is used, such as cosmetic products. Preferably the UV-protector according to the invention is in the form of solid particles having a mean diameter of 30–5000 μm, preferably approx. 50–3000 μm. In this context it is important to note that the solid UV-protector according to the present invention differs from, for example, a solid UV-protector coated with wax or some other substance in that it is in the form of solid particles so large that the particle material is made up, dispersed in wax, of a pigment reducing the penetration of UV light.

The solid UV-protector according to the invention is thus made up of a wax with a pigment reducing the penetration of UV light dispersed in it. Wax is the common name of substances which are waxy in their physical properties. By wax is in general meant a naturally and/or synthetically produced substance the properties of which at 20° C. range from solid but moldable to brittle and hard, from coarse to fine-grained, from transparent to opaque, but it is not glass-like. It melts without decomposing at a temperature above 40° C., having a relatively low viscosity even at a point somewhat above the melting or congealing point. Its solidity and solubility are often strongly dependent on the temperature.

Waxes differ from other solid natural and synthetic products mainly in that they usually melt and obtain low viscosity even within a temperature range of 50°–90° C., exceptionally up to a temperature of 200° C. They usually burn evenly and give surfaces treated with them a durable sheen.

According to one embodiment of the invention, the wax is at room temperature a solid, waxy substance which becomes fluid at 40° C. minimum, preferably at 50° C. minimum, and most preferably at 55° C. minimum. On the other hand, according to one embodiment the wax is at room temperature a solid, waxy-substance which becomes fluid at 200° C. maximum, preferably at 50° C. maximum, most preferably at 100° C. maximum. If the wax component according to the invention, or a dispersion thereof and a pigment reducing the penetration of UV light, melts at a temperature below 40° C., it is necessary to use with that wax other waxes or waxy components by means of which the melting temperature in the mixture dispersion can be raised to above 40° C., preferably above 50° C., and most preferably above 55° C.

Waxes can be classified into natural waxes, which also include waxes of mineral origin, and synthetic waxes, which also include chemically modified natural waxes.

Usable waxes according to the invention include those presented in the CRC Handbook of Chemistry and Physics, The Chemical Rubber Company, 53rd Ed. 1972-3, page C-753. This work is appended hereto as a reference. Suitable vegetable waxes include carnauba, candelilla, Japan wax and jojoba wax; animal waxes include beeswax, spermaceti wax, and lanolin wax; and mineral waxes include paraffin wax, ceresin wax, ozocerite, montan wax, and microcrystalline waxes.

Synthetic waxes according to the invention include unsaponifiable waxes prepared from natural ester waxes by decarboxylation, synthetically prepared hydrocarbon waxes such as polyethylene waxes and/or propylene waxes and polyethylene and polypropylene waxes modified by oxidation or by copolymerization with polar monomers, emulsifiable ester waxes formed from long-chain fatty alcohols and long-chain carboxylic acids, hydrogenated waxes obtained by hydrogenating drying oils such as castor oil, polyethylene oxide wax, polyethylene oxide/propylene oxide wax, phthalic imide wax and other waxy synthetic polymers, waxes made from saturated fatty acids by amide or imide condensation, and silicon waxes.

The waxes according to the invention also include waxy $C_{12}$–$C_{24}$ chain solid fatty acids, di- and polycarboxylic acids and corresponding alcohols, e.g. lauric, myristinic, palmitic, stearic, hydroxystearic, arachinic, behenic and erucic acids. Especially preferred natural waxes are carnauba wax, candelilla wax, jojoba wax, hydrogenated jojoba wax and Japan wax, beeswax, and/or lanolin. A preferred mineral or synthetic wax is paraffin wax. Other preferred waxes include cetyl palmitate, arachidyl behenate, behenyl erocant, pentaerythritol tetra-stearate, glycol-distearate, and cetostearyl stearate.

The wax used in a solid UV-protector according to the invention may also be a waxy surfactant, which include non-ionic waxy surfactants such as the reaction products of fatty alcohols having 10–22 carbon atoms in their alkyl chain, such as layryl, cetyl and stearyl alcohols, with ethylene oxide (1–50 ethylene oxide units/alcohol), the fatty acid esters of ethoxylated fatty alcohols, ethoxylated glycerides such as ethoxylated glyceryl monostearate, ethoxylated sterols and the like such as ethoxylated cholesterol, and ethoxylated lanolin and its derivatives. Other waxes include anionic waxy surfactants such as the salts of long-chain fatty acids and long-chain dicarboxylic acids, long-chain alkyl sulfates; polyethoxylated anionic surfactants such as polyethoxylated alcohol sulfates, sodium cocoyl cetionate, polyethoxylated phosphoric acid esters; N-acyl sarcosinates; polyethoxylated phosphate esters; taurates; salts of fatty acid esters and hydroxycarboxylic acid esters, such as Na and Ca stearoyl lactylates.

Further waxes include cationic, amphoteric or zwitterionic waxy surfactants and waxy salts formed by anionic and cationic components with each other. These include waxy phospholipids such as lecithin and its derivatives, imidazoline and betaine derivatives, alkyl amines, and alkyl ammonium compounds, polyethoxylated amines, and pyridinium salts.

Waxes used in a solid UV-protector according to the invention also include salts formed by anionic and cationic surfactants and polymers with each other, used either without other waxy components or in mixtures with other waxy components. By means of such "ancat" compounds it is possible to affect the structure of the wax and of the products formulated from it and their adherence to a base, such as skin in the case of cosmetic products. Such waxes can be prepared in different ways.

The following method is especially suitable for the preparation of salts of anionic and cationic surfactants and polymers in the form of an inorganic salt. In the method, the anionic and cationic components are dissolved separately in water, whereafter the solutions are combined. The formed "ancat" salt is separated from the aqueous solution by a suitable procedure, for example by filtering or washing with water clean of the initial components, or preferably by extracting in an organic solvent, whereupon the inorganic counter-ions of the initial components remain in the aqueous solution. The organic solvent can be removed, for example, by distillation.

In another method for the preparation of "ancat" waxes, the anionic component and the cationic component are dissolved separately in a suitable solvent. The solutions are combined and the precipitated "ancat" product is separated, for example, by filtration.

Combination waxes of a basic wax component and an acid wax component may also be used. The components are either melted together, or they are melted separately into another molten wax component, such as a melt of paraffin wax or a surfactant, and are then combined.

According to one embodiment of the invention, the solid UV-protector contains wax at minimum 15% by weight, preferably at minimum 20% by weight, and most preferably at minimum 30% by weight. According to one embodiment, the solid UV-protector according to the invention contains wax at maximum 90% by weight, preferably at maximum 75% by weight, and most preferably at maximum 63% by weight.

The dispersing of the UV-pigment into the melt of a waxy substance according to the invention may preferably take place without specific dispersing agents, if the UV-pigment is coated with a coating agent especially well suited for the medium used. In order to obtain a maximally homogenous dispersion it is often preferable to use a suitable dispersing agent. Its type depends on the properties of the wax used as the medium, for example its polarity. When non-polar or only slightly polar waxes were used as the medium, surprisingly good results were obtained with W/O type emulsifiers. By means of these it proved to be possible to disperse into wax both UV-pigments which had been pretreated to make them hydrophobic and those pretreated to make them hydrophilic, both together and separately. This surprising observation is perhaps explained in part by the fact that it is not necessary to require a molten dispersion to have as long stability periods in molten state as are required of a dispersion made in a liquid phase, such as an oil or aqueous phase. It is preferable to freeze a molten dispersion and to granulate it, without a long storage period, and thus the dispersion is obtained rapidly in a solid, storage-stabile form.

Examples of usable emulsifiers include the esters of alcohol or a polyhydroxide compound with fatty acids, e.g. fatty acids which contain 8–22 C atoms and preferably at minimum 12 C atoms in their alkyl chain, such as solid or waxy esters of lauric, cetanic, and stearic acids with ethylene glycol, polyethylene glycol, glycerol, polyglycerol, sorbitol, sucrose, pentaerythritol, and other polyols. Preferred emulsifiers include the mono- and diglycerides of such fatty acids, the sorbitol esters of the fatty acids and their ethoxylates, diacetylated fatty acid monoglyceride tartrates, fatty acid lactylates, fatty acid polyglycerol esters, fatty acid propylene glycol esters, fatty acid sucrose esters, and the acetic acid, lactic acid, citric acid and tartaric acid esters of fatty acid monoglycerides. Especially preferred dispersing agents include the monoglycerides of fatty acids containing at minimum 18 C atoms, and their acetic acid, lactic acid, citric acid and tartaric acid esters. Such emulsifiers are in general non-hazardous to the environment. They are usually of food grade, but are, nevertheless, not especially vulnerable to microbial action.

Usable dispersing agents include A—B—A block polymers, B standing for a functional group or polymer capable of being adsorbed to the pigment surface and A for a polymer chain well soluble in the medium, or dispersing agents of the "comb polymer" type, which have secondary chains well soluble in the medium and affixed to a polymer chain capable of being adsorbed to the pigment surface. A chain soluble in molten hydrophobic wax may in this case consist of, for example, polyhydroxycarboxylic acid or polymetacrylate and the chain adsorbing to the pigment surface may consist of polyethylene oxide or polyacrylate or a polyacrylate-rich copolymer.

A suitable amount of dispersing agent, in case the pigment is not sufficiently well dispersible into the wax used without a dispersing agent, is approx. 0.5% by weight, preferably at minimum approx. 2% by weight, of the amount of the UV-pigment. At the upper limit of the dispersing agent amount the medium consists entirely of a waxy emulsifier and/or dispersing agent, in which case the solid dispersion is made up of 10–80 parts by weight UV of pigment in 90-20 parts by weight of waxy emulsifier or dispersing agent.

In one preferred embodiment of the invention the weight ratio of the wax to the waxy emulsifier and/or dispersing agent in solid UV-pigment dispersions is approx. 50:1–1:1, preferably approx. 10:1–2:1.

According to one further embodiment of the invention, the waxy emulsifier and/or dispersing agent is made up of hydrophilic waxy surfactants which yield a solid UV-pigment dispersion. These include polyethoxylated non-ionic surfactants, such as the waxy reaction products of fatty alcohols having 8–22 C atoms in their alkyl chain, such as lauryl, cetyl and stearyl alcohols, with ethylene oxide; the fatty acid esters of polyethoxylated fatty alcohols; polyethoxylated glycerides, such as polyethoxylated glyceryl monostearate; polyethoxylated alcohol and polyalcohol esters such as polyethoxylated propyleneglycol monostearate, polyethoxylated glyceryl monostearate, polyethoxylated fatty acid esters of sorbitan; polyethoxylated sterols and corresponding compounds, such as polyethoxylated cholesterol and polyethoxylated lanolin and their derivatives; solid block polymers of polyethylene oxide and polypropylene oxide and solid polypropylene oxide/polyethylene oxide derivatives of ethylene diamine, octyl or nonylphenyl polyethoxylates, taurates.

When a hydrophilic emulsifier and/or dispersing agent is used, a preferred weight ratio of wax to emulsifier is approx. 0:1–1:1.

The solid protector against UV according to the invention may, in addition to a pigment reducing the penetration of UV light, wax, and possible dispersing agent, also contain additives. Such additives include color and mother-of-pearl pigments, melanin, radical scavenger compounds and vitamins, used either as admixtures or as powdering auxiliaries. It is also possible to add small amounts of oil or oily cosmetic auxiliary agents, as long as the lowering of the melting point caused by them is corrected by means of formulation.

The lowering of the melting point of a solid UV-protector according to the invention can be inhibited by mixing in a wax which raises the melting point, such as a microcrystalline wax or, if the protector contains oil, a wax which binds oil well, such as ozocerite, or a component which reinforces the structure, for example an "ancat" compound such as mentioned above or a long-chain alcohol.

According to one preferred embodiment of the invention, the solid protector against UV is a cosmetic, or it is used by precipitating it as part of a cosmetic, in which case the pigment transparent to UV and the wax are cosmetically acceptable substances. One important viewpoint in the invention is that new, easily handled products can be used for satisfying the world's increasing need for cosmetic protectors against UV light. According to one preferred embodiment, the UV-protector according to the invention, which is at the same time a cosmetic substance or a component of a cosmetic substance, contains at least one of the following cosmetic auxiliaries: a cosmetically acceptable organic protector against UV, a cosmetically acceptable preservative, a cosmetically acceptable antioxidant, and a cosmetically acceptable perfume. Typical protectors against UV include organic UV-protectors such as 4-aminobenzoic acid, NNN-trimethyl-4-(2-oxoborn-3-yldene-methyl)-anilinemethyl sulfate, homosalate, oxybenzone, 2-phenylbenzimidazole-5-sulfonic acid and its potassium, sodium and trimethanolamine salts, 3,3'-(1,4-phenylenedimethydyn)bis(7,7-dimethyl-2-oxobicyclo)2,2,1 (heptane-1-methanesulfonic acid) and salts, and 1-(4-tert.butylphenyl)-3-(4-methoxyphenyl) propane-1,3-dione. When the components of a solid protector against UV according to the invention are used, it should be borne in mind that they must be non-irritating and non-toxic and that they must fulfil the requirements set on cosmetic products in the legislation regarding cosmetic products. Methyl-butene parabene is an example of cosmetic preservatives to be mentioned. Butylated hydroxyanisol is an example of cosmetic antioxidants to be mentioned.

The invention also relates to a process for the preparation of any of the solid UV-protectors described above. An easily handled and practical solid protector against UV is obtained:

a) by dispersing into 90-20 parts by weight of molten wax 10–80 parts by weight of a pigment which reduces the penetration of UV light and consists of metal oxide particles having a mean primary particle diameter smaller than 0.150 μm, and b) by converting the molten or solid dispersion obtained from step a) into the form of solid particles having a mean diameter of at minimum 10 μm. The ingredients usable in the process according to the invention were discussed above in connection with the description of the protector against UV.

In the invention, the above-mentioned problems associated with UV-pigments are thus eliminated by formulating a solid protector against UV in the form of solid particles by first dispersing, and possibly grinding, a fine-grained UV-pigment at an elevated temperature into waxes which are liquid at that temperature but solid at room temperature, and by then cooling and granulating the obtained dispersion. In the preparation it is, of course, possible to use the kneading technique, in which case the raising of the temperature is not necessary, as long as sufficient mixing time is used to ensure the dispersing of the UV-pigment.

A product prepared in the manner described above will not produce dust, and it is easy to store and use. It is a further advantage that the use of a specific dispersing agent is not always necessary for achieving a storage stabile concentrate. The wax medium is selected on the basis of the surface properties of the formulated pigment reducing the penetration of UV light, the other components desired in the final product, and the desired oil or water extension of the final product, and other factors.

The preparation of granules according to the invention, containing UV-pigment, takes place by dispersing the UV-pigment or pigments into a melted wax component, and by cooling and granulating the dispersion. It is possible to use in the dispersing any device known from other pigment dispersion processes. When the aim is the highest UV-pigment concentrations, it is advantageous to use slow-moving kneading devices and roll mechanisms suitable for the dispersing of stiff mixes. Dispersing devices of high shear strengths or ultrasound devices are suitable for more viscous mixes. The dispersing may also be carried out by using grinding devices, such as a bead mill. In the dispersion step it is usually advantageous to use as an aid a suitable surfactant or a suitable combination of surfactants, preferably a mono- or diester of glycerol. When the agglomerates of the UV-pigments have been divided, the dispersion is allowed to solidify either into large pieces, such as sheets, pellets, tablets, extruder granules, or prills, which can, when so desired, be converted into a smaller particle size by a known method such as crushing, grinding or screening.

In one preferred embodiment of the invention, spray cooling is used for the solidification, in which case the dispersion is obtained either directly or after possible pulverization and/or screening, in the desired product form. Spray cooling takes place in the same manner as currently in other arts, such as the preparation of surfactants. The apparatus includes an atomizer by means of which the molten dispersion is converted into droplets, and a chamber in which the drops congeal in so solid a form that they will not adhere to the base. It possibly also includes a cyclone in which the product is separated from the gaseous medium used in the cooling, the medium normally being air. The temperature of the cooling gas must be below the congealing temperature of the melt, and may in general be close to the ambient temperature. The apparatus may be a cylindrical container which has the atomizer in its upper section and on the bottom of which the solidified particles will fall.

The atomizer may be a nozzle in which the molten dispersion is atomized either by pumping melt into the nozzle or by using as aid pressurized gas, such as compressed air. Furthermore, the atomization can be effected by a rapidly rotating dispersing device, such as a smooth or grooved plate, a wheel disc or a blade wheel, or a perforated cylindrical-surfaced prilling device. The molten dispersion is fed in at so high a temperature that the heat carried in it will suffice to keep the temperature of the feeding device above the congealing temperature of the melt dispersion, or the feeding device may also be equipped with a heating device, for example an electric resistor, hot-air blower, a liquid or steam mantle, etc.

The granules produced are preferably screened to the desired particle size. To avoid agglomeration of the product during storage, the granules may be powdered with a fine-grained material such as silica or silicic acid. Another preferred powdering substance is UV-pigment, although its efficiency in inhibiting agglomeration is usually not of the same order as that of silica. The amount of powdering substance depends on the softness of the granule and on at how high a temperature the product must be capable of being stored. A commonly used amount is approx. 0.01–2% of the weight of the granule. It is often preferable to carry out the powdering while the granules are warm, for example close to their maximum storage temperature.

Solid dispersions according to the invention may be turned into tablets by using devices which are used for tabletting waxy substances. In these, the mix to be tabletted may, for example, be cast onto a cooled perforated belt or cylinder, where the tablet is formed, and they may have a cooled belt conveyor on which the tablet will have time to harden. The tablet size may vary greatly, but a size of approx. 4–5 mm is preferable.

The use of solid UV-protectors according to the invention for the preparation of cosmetic formulations, such as sunscreen emulsions and creams, lipsticks, and hair-care products takes place simply by heating them to so high a temperature that the solid UV-pigment dispersion melts, whereupon it can be mixed with the other components to be used in the formulation, in the same manner as the waxy substance used as the medium of the dispersion would even otherwise be used separately for the said application.

Except in cosmetic applications, granules according to the invention may also be used in coatings and plastics products to which UV-pigment is added to improve their resistance to light. In these applications, the amounts UV-pigments used are usually small, for example 0.05–0.5% by weight. In UV-pigment granules according to the invention, intended for these applications, it is preferable to use as the wax component waxes or softeners which are even otherwise used in the coating or plastic concerned.

The following agents used in the examples are solid emulsifiers manufactured by Grindsted A/S: Dimodan: monoglyceride, distilled; Lactodan: lactic acid ester of monoglyceride; Panodan: diacetyl tartrate of monoglyceride; Artodan: Na and Ca stearoyl lactates containing lactic acid 20–34%; Famodan: sorbitan ester of fatty acid; Emuldan: mono/diester of fatty acid.

EXAMPLES

In the formulae of the examples, all percentages refer to % by weight. The granule samples were prepared by the following methods.

Granulation Method 1

The waxy ingredients were mixed with each other and were melted by heating. UV-pigment was mixed in gradually. Then the mixture was dispersed for 0.5–2 min by using a high-efficiency rod disperser, whereafter the obtained dispersion was poured onto a slab to cool into sheet form. The sheet was crushed and ground, was cooled, when necessary, before grinding, and was screened to the desired particle size.

Granulation Method 2

A molten dispersion was prepared as above, but the dispersing was carried out in the course of approx. 15–30 min by using a circular disperser blade. The molten dispersion was granulated in a rapidly rotating atomizer into droplets, which upon cooling in air hardened into round granules. The granules were screened to the desired particle size.

Example 1

A Nonionic Surfactant (Solan E)/hydrophilic UV—$TiO_2$

Into 200 g of molten PEG-75 lanolin (Solan E/Croda Chemicals, HLB approx. 16) there was dispersed 170 g of UV—Titan M212 which had been given a hydrophilic surface treatment. The UV—$TiO_2$ concentration in the mixture was 45.9%. The product was granulated with good results by both method 1 and method 2. The functioning of the product was ascertained in a cosmetic preparation.

Example 2

UV—$TiO_2$ 64%, Solan E

Into molten PEG-75 lanolin (Solan E/Croda Chemicals) there was dispersed UV—Titan M262 which had been given a hydrophobic coating, whereupon the UV—$TiO_2$ concentration of the dispersion was 64%. The granulation was by method 1.

Example 3

Nonionic Surfactant Solan E/hydrophobic UV—$TiO_2$

Into 200 g of molten PEG-75 lanolin (Solan E/Croda Chemicals) there was dispersed 170 g of UV—Titan M262 which had been rendered hydrophobic by a surface treatment. The UV—$TiO_2$ concentration of the mixture was 45.9%. The product was granulated with good results both by method 1 and by method 2. The functioning of the product was ascertained in a cosmetic preparation.

Example 4

Various Nonionic Surfactants

Solid dispersions containing UV—Titan M262 40% and UV—Titan M212 40% were prepared by method 1 in the following media: a propyleneoxy-ethyleneoxide derivative of ethylene diamine (Tetronic 908), Poloxamer 338, Poloxamer 407, polyoxyethylene(20) tallow fatty alcohol and polyoxyethylene (50) tallow fatty alcohol. The melt viscosities obtained with the ethoxylated fatty alcohols were so low that these dispersions were assessed to be suitable also for granulation method 2.

Example 5

Surfactant Acidan-N12, Melting in a Microwave Oven 40 g of Acidan N12 (a citric acid ester of monoglyceride, HLB approx. 11) and 40 g of UV—Titan were mixed while dry. 10 g of ion-exchanged water was added. The mixture was melted in a microwave oven, most of the water evaporating. The obtained viscous paste was stirred vigorously and was poured onto a slab, on which it was shaped into a sheet approx. 3 mm thick. The sheet was hardened by cooling, was crushed, and was screened with a 1-mm mesh screen.

Examples 6a–6c 40 parts by weight of hydrophobic UV—Titan M262 was dispersed into 60 parts by weight of a melt which had been prepared by heating together at approx. 110° C. for approx. 20 min the following components: Marlophor T (waxy polyethoxylated alkyl ester of phosphoric acid), Noram S (waxy alkylamine) and paraffin wax.

Example 6a: Marlophor:Noram=2:1

Example 6b: Marlophor:Noram=1:1

Example 6c: Marlophor:Noram:paraffin wax=1:1:1.

The viscosities of the melt dispersions were so low that they were assessed to be suitable for granulation by granulation method 2.

Example 7

"Ancat" 1

"Ancat" compound dodecyltrimethylammoniumdodecyl sulfate was prepared by dissolving separately in water equal molar amounts of sodium dodecyl sulfate and dodecyltrimethylammonium bromide, by combining the solutions, by extracting the "ancat" salt with diethyl ether, and finally by evaporating the ether. The obtained fine-grained solid compound was added to molten paraffin, into which it dispersed, increasing the viscosity of the melt even when used in a dose of a few per cent.

Example 8

"Ancat" 2

An "ancat" compound was prepared by dissolving in diethyl ether separately equal molar amounts of laurinic acid and dodecylamine. By combining the solutions a precipitate was obtained, which was separated by filtration. The remainder of the solvent was dried off by evaporation.

The obtained fine-grained "ancat" salt was added on a hot plate into molten paraffin, in which it dissolved well. The adding was continued until a 1:1 mixture with paraffin was obtained. Then UV—Titan M262 was dispersed into this approximately 100° C. melt until a mixture containing UV—TiO$_2$ 45% was obtained, which mixture was cast onto a slab to form a sheet, which upon cooling was easily crushed into granules.

Example 9

"Ancat" 2, Further Experiment

The "ancat" compound of Example 9 was melted as such on a hot plate, and the melt was heated to approx. 100° C. UV—Titan M262 was dispersed into the melt until a mixture containing UV—TiO$_2$ 45% was obtained. This mixture was cast onto a slab to form a sheet, which upon cooling was easily crushed into granules.

Example 10

Wax+Cetyl Alcohol, No Dispersing Agent

A melt was prepared which contained 52 g of paraffin wax, 4 g of beeswax and 2 g of cetyl alcohol (Crodacol C-90/Croda Chemicals). 42 g of UV—Titan M262 was dispersed into the mixture.

The obtained dispersion was granulated by method 1.

Example 11

Dispersing Agent 14.7% Lactodan B30, Hydrophobic UV—TiO$_2$ 360 g of paraffin wax, 30 g of beeswax, and 150 g of surfactant Lactodan B30 were melted at approx. 100° C. Into this melt there was dispersed 480 g of hydrophobic UV—Titan M262, whereupon the UV—TiO$_2$ content of the dispersion was 47%. The mixture was granulated by method 2, with good results.

Example 12

Dispersing Agent Lactodan B30 20%, Various Wax Components

Different waxes were experimented with in granulation according to method 1. Good results were obtained with all of the formulae.

|  | Example |  |  |  |  |  |
|---|---|---|---|---|---|---|
|  | 12a | 12b | 12c | 12d | 12e | 12f |
| Lactodan B30 | 20 | 20 | 20 | 20 | 20 | 20 |
| Paraffin wax | 30 | 30 | 30 | — | — | 15 |
| Beeswax | 5 | — | — | — | — | 10 |
| Carnauba wax | — | 5 | — | 35 | 35 | 10 |
| Candelilla wax | — | — | 5 | — | — | — |
| UV-Titan M262 | 45 | 45 | 45 | 45 | — | 45 |
| UV-Titan M212 | — | — | — | — | 45 | — |

Example 13

Dispersing Agent Lactodan 1.8%; Testing in Cosmetic Preparations

A molten approx. 80° C. UV—TiO$_2$ dispersion was prepared, which contained paraffin wax 48.2%, beeswax 3.8%, Lactodan B30 1.8%, and UV—Titan M262 46.5%. The mixture was dispersed by using an Ultra-Turrax disperser and was granulated by using a cylindrical prilling device rotating at 1400 r/min. Its 5 mm high cylindrical surface was equipped with 0.7 mm diameter perforations, its 200 mm diameter lower surface was closed, and its upper surface was open in the center for the feeding in of the melt dispersion. The molten dispersion solidified in the air chamber into round particles having an average particle size of approx. 0.5 mm.

Granules made according to the formula of Example 13, from which particles having a size greater than 0.83 mm had been removed by screening, were tested for cosmetic preparations, with the following results:

The sun protection factor of a gloss lip-care rouge without the addition was low, 3, and its UVA:UVB ratio was mediocre, 0.54. When granules (0.9% UV—TiO$_2$) in an amount of 2% were dispersed into the gloss rouge mix, the value of the sun protection factor rose to 6 and the UVA:UVB ratio to an excellent level, 0.69.

The sun protection factor of lipstick without the addition was mediocre, 4–5, whereas with a granule amount of 4% (1.8% UV—TiO$_2$) the coefficient rose to a level of 16–19.

A sun-protector cream was prepared by using granules (4.9% UV—TiO$_2$) in an amount of 10.6%. The sun protection factor was at a level of 29–31.

Example 14

UV—TiO$_2$ 71%, Lactodan B30

Into a melt which contained 25 g of paraffin wax, 5 g of carnauba wax and 15 g of Lactodan B30 there was dispersed 110 g of hydrophobically coated UV—Titan M262, whereupon the UV—TiO$_2$ concentration in the mix was 71.0%. After prolonged kneading at a low speed, a clear-surfaced homogenous dispersion was obtained. Granules were prepared by method 1.

Example 15

UV—TiO$_2$ was dispersed into molten wax/emulsifier mixtures 15a)–15f). Dispersions were obtained the viscosities of which were suitable for both granulation methods 1 and 2.

|  | Example: |  |  |  |  |  |
|---|---|---|---|---|---|---|
|  | 15a | 15b | 15c | 15d | 15e | f |
| Lactodan P22 | 20 | — | — | — | — | — |
| Artodan AM | — | 20 | — | — | — | — |
| Panodan AM | — | — | 20 | — | — | — |
| Famodan MS | — | — | — | 5 | — | — |
| Dimodan PV | — | — | — | — | 1 | — |
| Emuldan HA40 | — | — | — | — | — | 1 |
| Paraffin wax | 35 | 35 | 35 | 15 | 24 | 24 |
| Carnauba wax | — | — | — | — | 2 | 2 |
| UV-Titan M262 | 45 | 45 | 45 | 45 | 23 | 23 |

Example 16a–16c 45 parts by weight of hydrophobic UV—Titan M262 was dispersed into melt mixtures which contained 46 parts by weight of paraffin wax, 4 parts of beeswax and 5 parts of the following emulsifiers:

Example 16a) Artodan CF 40

Example 16b) Artodan CP 80

Example 16c) Artodan NP 55

Well spreading melt dispersions were obtained, which were assessed to be suitable for both granulation methods 1 and 2.

Example 17

A Mixed Granule of Hydrophobic and Hydrophilic UV—$TiO_2$

Granules were prepared by using as the raw materials paraffin wax 23.8%, carnauba wax 4.8%, Lactodan B30 14.3%, UV—Titan M262 28.6%. and UV—Titan M212 28.6%. The UV—$TiO_2$ concentration in the mix was 57.2%.

Example 18

Compatibility of Hydrophobic and Hydrophilic UV—$TiO_2$

Granules were prepared by method 1 by dispersing 45 g of hydrophobic UV—Titan M262 into a melt consisting of 20 g of Lactodan B30 and 35 g of paraffin wax. Another batch of corresponding granules was prepared by using hydrophilic UV—Titan M212. The mutual compatibility of these granules was tested by first mixing them together and by then melting this mixture. A well flowing, beautiful dispersion was obtained.

Example 19

The following UV-pigments were mixed with a 100° C. wax melt which consisted of mixtures of paraffin wax, beeswax and Lactodan B30 at the weight ratio 30:5:20:

Example 19a) UV—ZnO (Sachtotec LA 10)

Example 19b) UV—ZnO+UV—Titan M262 1:1

Example 19c) UV—Titan M262

The zinc oxide dispersed into the wax melt, forming a low-viscosity mixture, whereupon the UV-pigment concentration in mixture a) was 50.3% by weight. The corresponding UV-pigment concentrations in mixtures b) and c) were 45% by weight. The mixtures were dispersed for 1 min by means of an Ystral rod disperser and they were cast into sheets. The cooled sheets were crushed, were ground in a Philips coffee grinder, and particles larger than 0.84 mm were screened off.

Example 20

The functioning of the granules of Example 19 was tested in a W/O sunscreen emulsion. The oil phase of the emulsion was made up of the following components: Arlacel 780 (PEG3/PPG2/-Glyceryl/Sorbitol/Hydroxystearate/Isostearate) 4.0 parts by weight, mineral oil 12 parts by weight, Miglyol 812 (Caprylic/Capric Triglyceride) 6 parts by weight, Crill 6 (Sorbitan Isostearate) 2 parts by weight, and UV-pigment granules in case a) 8.9 parts by weight and in cases b) and c) 10.6 parts by weight. The aqueous phase of the emulsion consisted of sorbitol 1.25 parts by weight, propylene glycol 1.25 parts by weight, Mg sulfate 0.7 parts by weight, and water in case a) 63.65 parts by weight and in cases b) and c) 61.95 parts by weight. Both the oil phase and the aqueous phase were heated to 75° C. The aqueous phases were added to the oil phases gradually, while mixing. Finally 0.25 parts by weight of perfluoro-polymethyl-isopropyl ether (Fomblin HC/25) was added.

The functioning as a protector against UV light of these emulsions which contained UV-pigment approx. 5% by weight was tested, with the following results:

| Sample | UV protection factor (SPF in vitro, FDA) |
|---|---|
| 19a) | 3 |
| 19b) | 16–19 |
| 19c) | 17–20 |

The granules 19b), containing UV—ZnO and UV—$TiO_2$, and the granules 19c), containing UV—$TiO_2$, yielded excellent protection results. It can also be seen that the result obtained with the combination granule 19b) was unexpectedly good as compared with the results obtained with the granules 19a) and 19c), which contained only UV—ZnO or only UV—$TiO_2$.

Example 21

Solid dispersions were prepared from UV—Titan M160, which is a rutile pigment strongly surface modified with aluminum oxide and stearic acid. The pigment dispersed easily into ester waxes, such as carnauba wax, or into mixtures of such waxes and paraffin waxes. The following solid dispersions were prepared:

| | Example: | | |
|---|---|---|---|
| | 21a) | 21b) | 21c) |
| Carnauba wax | 50 | 25 | 5 |
| Candelilla wax | — | 25 | — |
| Paraffin wax | — | — | 50 |
| UV-Titan M160 | 50 | 50 | 45 |

The dispersing was successful. Dispersions 21a) and 21b) were granulated by method 1, dispersion 21c) by both method 1 and method 2.

Example 22

The solid UV—Titan M160 dispersion of Example 21c) was used for making a test emulsion having a UV—Titan M160 concentration of 5%. The in vitro sun protection factor measured for the preparation was 23–27 (FDA) and its UV-A/UV-B ratio 0.66. The dispersing was successful. Dispersions 22a) and 22b) were granulated by method 1, dispersion 22c) by both method 1 and method or alternatively dispersions 22a) and 22b) were tabletted.

We claim:

1. A solid protector against UV light, comprising 10–80 parts by weight of a pigment and 90-20 parts by weight of a wax, wherein said pigment is made of metal oxide particles having a mean primary particle diameter smaller than 0.150 µm, reduces the penetration of UV light and is dispersed in said wax, and said protector is in the form of solid particles having a mean diameter of at minimum 10 µm.

2. The protector against UV light according to claim 1, wherein the pigment reducing the penetration of UV light is made up of metal oxide particles having a mean primary particle diameter of 0.010–0.100 µm.

3. The protector against UV light according to claim 1, wherein the pigment reducing the penetration of UV light is made up of titanium dioxide ($TiO_2$) particles or zinc oxide (ZnO) particles or a mixture thereof.

4. The protector against UV light according to claim 1, wherein the protector contains at minimum 36% by weight of said pigment reducing the penetration UV light.

5. The protector against UV light according to claim 1, wherein the protector contains at maximum 85% by weight of said pigment reducing the penetration of UV light.

6. The protector against UV light according to claim 1, wherein the protector is in the form of particles having a mean diameter of 30–5000 μm.

7. The protector against UV light according to claim 1, wherein the wax is a substance which is solid and waxy at room temperature and becomes fluid at a temperature of at minimum 40° C.

8. The protector against UV light according to claim 7, wherein the wax is a substance which is solid and waxy at room temperature and becomes fluid at a temperature of at maximum 200° C.

9. The protector against UV light according to claim 1, wherein the wax is a natural wax, a mineral wax, or a mixture thereof.

10. The protector against UV light according to claim 1, wherein the wax is polyethoxylated alcohol or monoglycerol.

11. The protector against UV light according to claim 1, wherein the protector contains at minimum 15% by weight of said wax.

12. The protector against UV light according to claim 1, wherein the protector contains at maximum 90% by weight of said wax.

13. The protector against UV light according to claim 1, wherein the protector is a cosmetic or constitutes part of a cosmetic, and the pigment transparent to UV light and the wax are cosmetically acceptable substances.

14. The protector against UV light according to claim 13, wherein the protector contains at least one of the following cosmetic auxiliary substances: cosmetically acceptable organic protectors against UV light, cosmetically acceptable preservatives, antioxidants, vitamins and radical scavenger compounds, cosmetically acceptable color, mother-of-pearl and melanin pigments, and cosmetically acceptable perfumes.

15. A method for preparing the solid protector against UV light according to claim 1, which comprises the following steps:
   a) dispersing 10–80 parts by weight of a pigment which reduces the penetration of UV light and is made up of metal oxide particles having a mean primary particle diameter smaller than 0.150 μm, into 90-20 parts by weight of a molten or viscous wax, whereby a molten or solid dispersion is obtained, and
   b) converting the molten or solid dispersion obtained from step a) into the form of solid particles having a mean diameter of at minimum 10 μm.

16. The method according to claim 15, wherein said step a) of dispersing the pigment reducing the penetration of UV light into the wax is carried out with a kneading device or a roller mechanism if the wax is stiff, or a mixing device having a high shear speed or an ultrasound device if the wax is viscous, or a grinding device if a completely non-agglomerated pigment reducing the penetration of UV light is desired.

17. The method according to claim 15, wherein said step a) of dispersing the pigment reducing the penetration of UV light into the wax uses as an aid a surfactant.

18. The method according to claim 15, wherein said step b) comprises molding the molten or solid dispersion obtained from step a) into a form capable of being comminuted, hardening the molten or solid dispersion, when necessary, by cooling to below the congealing point of the wax, and comminuting the molten or solid dispersion by cutting, chopping, crushing or grinding.

19. The method according to claim 15, wherein step b) comprises converting the melt obtained from step a) into drops, and solidifying the drops by cooling to below the congealing point of the wax.

20. The method according to claim 15, further comprising c) screening the solid particles obtained from step b) to the desired size.

21. The method according to claim 15, further comprising d) coating the solid particles obtained from step b) with a powder which inhibits agglomeration.

22. The solid protector against UV light according to claim 1, wherein said protector is used as a component in cosmetic products.

23. The protector against UV light according to claim 2, wherein the pigment reducing the penetration of UV light is made up of metal oxide particles having a mean primary particle diameter of 0.020 μm.

24. The protector against UV light according to claim 3, wherein the pigment reducing the penetration of UV light is made up of titanium dioxide ($TiO_2$) particles.

25. The protector against UV light according to claim 4, wherein the protector contains at minimum 40% by weight of said pigment reducing the penetration UV light.

26. The protector against UV light according to claim 25, wherein the protector contains at minimum about 44% by weight of said pigment reducing the penetration UV light.

27. The protector against UV light according to claim 5, wherein the protector contains at maximum 80% by weight of said pigment reducing the penetration of UV light.

28. The protector against UV light according to claim 27, wherein the protector contains at maximum 75% by weight of said pigment reducing the penetration of UV light.

29. The protector against UV light according to claim 6, wherein the protector is in the form of particles having a mean diameter of about 50–3000 μm.

30. The protector against UV light according to claim 7, wherein the wax is a substance which is solid and waxy at room temperature and becomes fluid at a temperature of at minimum 50° C.

31. The protector against UV light according to claim 30, wherein the wax is a substance which is solid and waxy at room temperature and becomes fluid at a temperature of at minimum 55° C.

32. The protector against UV light according to claim 8, wherein the wax is a substance which is solid and waxy at room temperature and becomes fluid at a temperature of at maximum 150° C.

33. The protector against UV light according to claim 32, wherein the wax is a substance which is solid and waxy at room temperature and becomes fluid at a temperature of at maximum 100° C.

34. The protector against UV light according to claim 9, wherein the wax is paraffin wax, carnauba wax, candelilla wax, jojoba wax, Japan wax, beeswax, lanolin, or a mixture thereof.

35. The protector against UV light according to claim 9, wherein the wax is hardened (hydrogenated).

36. The protector against UV light according to claim 10, wherein the wax is an alcohol containing 12–22 carbon atoms in its chain, a polyethoxylated hydrogenated ricinic acid, a polyethoxylated lanolin, or a combination thereof.

37. The protector against UV light according to claim 11, wherein the protector contains at minimum 20% by weight of said wax.

38. The protector against UV light according to claim 37, wherein the protector contains at minimum 30% by weight of said wax.

39. The protector against UV light according to claim 12, wherein the protector contains at maximum 75% by weight of said wax.

40. The protector against UV light according to claim 39, wherein the protector contains at maximum 63% by weight of said wax.

41. The method according to claim 17, wherein said surfactant is an ester of a fatty acid with glycol, glycerol, polyglycerol or sorbitol.

42. The method according to claim 17, wherein said surfactant is a mono- or di-glyceride of a fatty acid, or an ester thereof with a small-molecule hydroxy acid.

43. The method according to claim 19, wherein said solidifying step is achieved by spray cooling, which comprises atomizing the molten or solid dispersion into droplets, cooling the droplets in air or gas into solid form, and recovering the solidified droplets.

44. The method according to claim 21, wherein said powder is silica or silicic acid.

45. The method according to claim 21, wherein said powder is a pigment reducing the penetration of UV.

46. The method according to claim 21, wherein the amount of the powder inhibiting agglomeration is 0.01–2% of the weight of the solid protector against UV light.

47. The solid protector against UV light according to claim 22, wherein the cosmetic products are sunscreen creams, lip pomades, or hair-care products.

* * * * *